United States Patent [19]
Worden et al.

[11] Patent Number: 6,022,727
[45] Date of Patent: Feb. 8, 2000

[54] METHOD FOR FORMING REVERSIBLE COLLOIDAL GAS OR LIQUID APHRONS AND COMPOSITIONS PRODUCED

[75] Inventors: Robert Mark Worden, Holt, Mich.; Alec B. Scranton, Boulder, Colo.

[73] Assignee: Board of Trustees Operating Michigan State University, East Lansing, Mich.

[21] Appl. No.: 09/005,939

[22] Filed: Jan. 12, 1998

[51] Int. Cl.⁷ .......................... B01D 53/62; B01J 13/00; C12N 1/34

[52] U.S. Cl. .................. 435/243; 95/150; 95/253; 210/643; 435/246; 435/262.5; 435/818; 435/821; 516/19; 516/64; 588/226

[58] Field of Search ................. 516/19, 64; 210/643; 95/253, 150; 525/330.1; 526/911; 588/226; 435/818, 821, 243

[56] References Cited

U.S. PATENT DOCUMENTS

| | | | |
|---|---|---|---|
| 3,718,609 | 2/1973 | Weimer | 516/19 X |
| 3,764,481 | 10/1973 | Muller | 435/818 X |
| 4,283,290 | 8/1981 | Davies | 210/643 |
| 4,486,333 | 12/1984 | Sebba | 516/19 X |
| 4,555,343 | 11/1985 | Bauer et al. | 210/643 |
| 4,836,939 | 6/1989 | Hendrickson | 516/19 X |
| 5,512,180 | 4/1996 | Ho | 210/643 |
| 5,593,593 | 1/1997 | Nilsen et al. | 210/643 X |
| 5,739,210 | 4/1998 | Scranton et al. | 525/330.1 X |

*Primary Examiner*—Richard D. Lovering
*Attorney, Agent, or Firm*—Ian C. McLeod

[57] ABSTRACT

A method for forming gas or liquid aphrons with reversible surfactants or emulsifiers is described. Polymers which change their emulsifying properties upon change of pH, temperature or other condition are used to form the aphrons. The aphrons are useful for chemical reactions and separations, mass transfer processes, and for biological processes.

21 Claims, 4 Drawing Sheets

METHOD FOR FORMING REVERSIBLE COLLOIDAL GAS OR LIQUID APHRONS AND COMPOSITIONS PRODUCED

BACKGROUND OF THE INVENTION (1) Field of the Invention

The present invention relates to a method of use of reversible polymeric surfactants or emulsifiers for forming colloidal gas aphrons (CGA) or colloidal liquid aphrons (CLA) and to the aphron compositions which are produced. The reversible CGA and CLA compare favorably with those made using conventional surfactants. The CGA and CLA are rapidly destabilized and coalesced by making small changes in the pH. The aphrons are used for transfer of chemicals to and from the aphrons. The reversible surfactants or emulsifiers are preferably nontoxic to microorganisms and suited for biotechnological applications involving living cells (e.g., fermentations). The CGA or CLA can particularly be used in a fluidized bed reactor.

(2) Description of Related Art

A. Separation Art

Many processes in the chemical, biochemical, and environmental industries involve phase-contacting operations in which one fluid phase is dispersed in a second immiscible fluid phase. The high interfacial area between the phases created by the dispersion allows rapid transfer of components from one phase to the other. Examples include gas-liquid and liquid-liquid reaction systems, solvent extraction, flotation, and gas scrubbing. The two phases can be dispersed mechanically, using equipment including stirred tanks, spray towers, and mixer-settlers. Surfactants or emulsifiers can also be used, both alone or in combination with mechanical methods, for generating and stabilizing dispersions. Once the transfer has taken place, it is often desirable to coalesce the dispersed phase and separate the two phases again.

Processes to treat radioactive, hazardous-chemical, and mixed wastes involve transfer of material from one phase to another. Such transfer operations are done to remove components of the waste for further characterization, to separate and/or concentrate particular waste fractions, or to add components needed to stabilize or remediate the wastes. Examples of such processes include extraction of organic wastes from aqueous liquids; stripping or absorption of gaseous components; flotation and foam fractionation for removal of colloidal materials, organic and metal ions from aqueous liquids; soil washing to eliminate hazardous wastes, and soil aeration to enhance bioremediation.

Often, the mass-transfer step is rate-limiting. In such instances, increasing the mass transfer rate directly increases the overall process efficiency. The rate of interphase mass transfer can be calculated as the product of three terms: the concentration difference (driving force) between the two phases, the mass-transfer coefficient, and the interfacial area per unit volume. In mass-transfer-limited systems, the concentration driving force is often small, because either the fluid from which the solute is transferring is dilute or the solubility of the transferring substance is low. The mass-transfer coefficient is weakly dependent on the chemical composition of the two phases and the local hydrodynamic conditions, and is difficult to adjust significantly. However, the interfacial area can vary by orders of magnitude. Extremely high interfacial areas can be produced by creating a fine dispersion of one phase in the other. Because the interfacial area per unit volume is inversely proportional to the average diameter of the dispersed phase, efforts to increase interphase mass-transfer rates generally focus on reduction of this diameter.

Mechanical agitation is often used for creating a dispersion of the phases. The shear forces generated through agitation overcome the surface tension and break up large droplets or bubbles into smaller ones. However, the resulting dispersion is thermodynamically unstable. To counteract the ongoing process of coalescence, the dispersion must be agitated continuously. Consequently, this approach is energy-intensive. It also does not scale up favorably. For similarly shaped mixing vessels, the power required to turn the impeller increases with the impeller diameter in the fifth power, whereas the reactor volume increases with the impeller diameter to the third power (McCabe et al., Unit Operations of Chemical Engineering, Fifth Ed. McGraw-Hill, New York, 350–357 (1993)).

Creation of a fine dispersion of one phase in the other can dramatically increase process efficiency. Colloidal gas aphrons (CGA) and colloidal liquid aphrons (CLA) have diameters ranging from submicron to over 100 microns and thus can provide exceedingly high interfacial areas for such applications (Matsushita et al., Colloids and Surfaces, 69:65–72 (1992)). Aphrons may have a surfactant-stabilized aqueous shell surrounding the gas or liquid droplet. Because surfactant molecules are amphipathic (i.e., they have both hydrophobic and hydrophilic regions), they accumulate at the interface between the phases and can reduce the surface tension. The surfactant molecules can generate an electric double layer that extends out from the interface and repels adjacent bubbles or droplets, thus stabilizing the dispersion against coalescence. This shell may also provide steric repulsion between adjacent aphrons, which stabilizes the aphrons against coalescence. CGA dispersions are easy and energy-efficient to produce, provide extremely high mass-transfer rates (Bredwell et al., Eighteenth Symposium on Biotechnology for Fuels and Chemicals, Gatlinburg, Tenn., May 5–9, (1996)), and can enhance the rate of bioremediation processes fed with synthesis gas (hydrogen and carbon monoxide), for instance. To date, the use of aphrons in commercial applications has been limited, because the stability imparted by the surfactant shell makes it difficult to break the dispersions and separate the phases following the phase-contacting step.

Sebba, F., Foams and Biliquid Foams-aphrons, John Wiley and Sons, New York, 62–71; 103–106 (1987) describes a CGA having colloidal dimensions on the order of 50 $\mu$m in diameter, encapsulated by a soapy water "shell" and immersed in a continuous aqueous phase. The CLA is described as an analogue of a CGA with the gas replaced by a similarly sized droplet of a second liquid phase. The shell is thought to be relatively thick compared to surfactant layer surrounding conventional bubbles. Amiri and Woodburn, Trans. IChemE 68(a) 154–160 (1990) have estimated the shell thickness to be about 0.75 $\mu$m for CGA. Both CGA and CLA dispersions are L:m. stable enough to be pumped with minimal coalescence from the device where they are formed to some remote site, where they are used. Extremely stable CLA suspensions have been stored in a stoppered bottle for years without evidence of deterioration. However, the degree of stabilization depends on the properties of the surfactant and the two phases.

The volumetric mass transfer rate (Q) is related to the mass-transfer coefficient (K), the interfacial surface area per unit volume ($\alpha$), and the concentration driving force ($\Delta C$) according to the following equation $$Q = K\alpha(\Delta C)$$

Although K and ΔC are often difficult to vary significantly, α is inversely proportional to the diameter of the dispersed phase. Thus, the small diameters of surfactant-stabilized aphron dispersions can yield extremely high Q values. It has been demonstrated that extremely high Kα values (800 to 1800 h$^{-1}$) could be obtained using CGA, even in an unagitated vessel (Bredwell et al., Eighteenth Symposium on Biotechnology for Fuels and Chemicals, Gatlinburg, Tenn., May 5–9 (1996).

Because they offer extremely high surface areas, CGA and CLA are being used increasingly to facilitate mass-transfer operations in chemical and environmental processes. CGA are used to supply oxygen to biological waste-treatment bioreactors. Other proposed applications for CGA include providing gaseous substrates for synthesis-gas fermentations (Bredwell, et al., Eighteenth Symposium on Biotechnology for Fuels and Chemicals, Gatlinburg, Tenn., May 5–9 (1996)) flotation of sulfur crystals from catalytic processing of natural gas (Amiri and Woodburn, Trans. IChemE 68(a), 154–160 (1990)), and soil washing (Roy et al., Separation Science and Technology 27(12) 1555–1568 (1992)). Proposed applications for CLA include extraction of enzymes from fermentation broth (Save et al., Biotechnology and Bioengineering 41:72–78 (1993)), immobilized-enzyme bioreactors (Lye et al., Biotechnology and Bioengineering 51:69–78 (1996)), stripping dilute solutes from aqueous phases and delivering apolar substrates to aqueous reaction systems.

A key problem which limits the applications for CGA and CLA is that the stability imparted by the surfactant hinders phase separation after the mass-transfer step is complete. In some cases, a destabilizing agent can be added to solubilize and break the dispersion. However, this approach adds complexity and cost to the process, and may necessitate additional separation steps to remove the destabilizing agent. Hence, there is a need for new methods to produce CGA and CLA that remain stable during the mass-transfer step, but afterwards can be rapidly coalesced.

The patent art has described a number of methods for forming microbubbles (polyaphrons) using a surface active agent (surfactant) in an aqueous liquid. Typically the microbubbles contain up to 65% gas, usually between 20% to 60% gas, as described by Sebba (U.S. Pat. No. 3,900,420). The half lives are 5 to 10 minutes for the soaps used by Sebba. The diameter of the microbubbles was between about 1 to 10 microns. Sebba (U.S. Pat. No. 4,486,333) describes biliquid polyaphrons using various surfactants by first forming gas polyaphrons and then adding a non-polar liquid. Michelsen and Sebba (U.S. Pat. No. 5,314,644) describe a particular apparatus for forming the microbubbles. Yoon et al (U.S. Pat. No. 4,981,582; fine particle flotation); Lu et al (U.S. Pat. No. 5,443,985; cell culture) and Schutt et al (U.S. Pat. No. 5,605,673; contrast agents). Other patents of general interest are U.S. Pat. Nos. 3,891,571 to Lambou et al; 4,684,479 to D'Arrigo et al; 4,668,632 to Young et al; 5,009,792 to Pettersen and 5,223,429 to Tepic relating to foams and their uses.

B. Polymer Art

There are a number of patents relating to reversible surfactants for a variety of non-microbubble applications. Some are reversible as a function of pH. U.S. Pat. No. 3,950,296 to Kangas et al describe surfactants used for coacervation (precipitation) of an ingredient in an aqueous solution. U.S. Pat. No. 4,735,731 to Rose et al describes pH sensitive thickening surfactants.

Polymeric emulsifiers and thickeners, which are surfactants, are well known. Polymeric emulsifiers have been used to stabilize oil droplets in water for a variety of applications including, but not limited to, aqueous cleaning operations, suspension polymerization, food applications, cosmetics, pharmacy, agriculture and bitumen processing. The emulsifiers generally contain both hydrophilic and hydrophobic groups, giving the polymer an "amphipathic" character. Examples of such polymeric emulsifiers and their properties are described in standard texts such as Irja Pirma, Polymeric Surfactants, Marcel Dekker, (1992). This text summarizes an extensive body of literature regarding hydrophilic/hydrophobic diblock, triblock, graft and random copolymers. Specific examples of polymeric emulsifiers are provided in Great Britain Patent GB 2,115,002A to Baker (1983), which discloses block or graft copolymers of hydrophobic monomers with hydrophilic monomers. U.S. Pat. No. 5,021,526 to Ball, describes random terpolymer emulsifiers made from water-soluble vinyl monomers, water-insoluble vinyl monomers containing 12 to 30 carbon atoms, and polymerizable acid monomers. In addition, hydrophobically functionalized crosslinked polyacrylic acid may be used as polymeric emulsifiers, as reported by R. Y. Lochhead ACS Symposium Series, Vol. 462, 101 (1991). In all of these examples, the molecular structure of the emulsifier contains both hydrophobic and hydrophilic groups to achieve an amphipathic nature. In general, the hydrophilic groups may be anionic, cationic or nonionic in nature. Furthermore, although there has been very limited discussion of polymeric emulsifiers which allow the emulsion to be reversibly formed and broken, as discussed in Great Britain Patent GB 2,006,744A to Sonnerqard (1979), no such emulsifiers which are truly effective have yet been obtained.

Alkali swellable or alkali soluble thickeners (AST's) have found wide application for thickening paint, coating, textile, consumer product, and adhesive formulations. In general, these thickeners exhibit low viscosity under acidic conditions, and high viscosity under basic conditions making them easy to manufacture and blend into formulations while providing excellent thickening properties in the final formulation upon pH adjustment. As described in several reviews and monographs (G. D. Shay, Advances in Chemistry, 223, 457 (1989) and Toshio Murakami, R. H. Fernando, J. E. Glass, Surface Coating International, 76, 8 (1993)), these thickeners are typically produced by emulsion polymerizations of acrylic or methacrylic acid with a hydrophobic monomer such as ethyl acrylate. The acid groups may be positioned on the surface of the resulting beads by semi-batch or multi-stage addition of the hydrophilic monomer in the latter stages of an emulsion polymerization such as described in U.S. Pat. Nos. 5,266,646 and 5,451,641 to Eisenhart. Generally, such polymers contain more than 40 wt. % of the hydrophobic monomer. For example, Murakami et al., teach compositions containing 48–51 wt. % of the hydrophobic monomer, Toshio Murakami, R. H. Fernando, J. E. Glass, Surface Coating International, 76, 8 (1993). Rodriguez and Wolfe report systems containing 66 wt. % of the hydrophobic ethyl acrylate monomer and 33 wt. % of the hydrophilic methylmethacrylate monomer, Macromolecules, 27, 6642 (1994). U.S. Pat. No. 4,351,754 to Duprey, teaches that at least 30% alkyl methacrylates with one to four carbon atoms must be used. U.S. Pat. No. 4,801,671 to Shay, teaches compositions with 15% to 50% carboxy monomer, 10% surfactant monomer, and the balance being a hydrophobic ethyl acrylate monomer. When utilizing high amounts of hydrophilic acid monomer, it is often necessary to include crosslinking agents to maintain insolubility and high thickening efficiency, Toshio Murakami, R. H. Fernando, J. E. Glass, Surface Coating International, 76, 8 (1993).

Water-insolubility of the emulsifiers and thickeners described above is provided via hydrophobic comonomers or functional groups such as aliphatic esters of acrylic or methacrylic acid. Polymeric emulsifiers also contain hydrophobic comonomers to impart compatibility with the emulsified oil phase, while thickeners contain hydrophobic comonomers to provide water insolubility at acidic pH. These classes of materials have never previously been made by aqueous emulsion or suspension polymerization without hydrophobic comonomers or hydrophobic functional groups.

Polymers which are sensitive to pH have been widely used in pharmaceutical and agricultural controlled-release formulations, see for example, Advances in Polymer Science, Vol. 122 Springer Verlag Berlin Heidelberg, 1995. In particular, such polymers have been used as coatings, and in particular, as enteric coatings. Typically, copolymers of hydrophilic carboxy or amine functional monomers with hydrophobic water-insoluble monomers are described for such coatings. These materials provide water-insoluble coatings at one pH, thereby preventing drug diffusion and release. At a second pH, the coatings become water-permeable or water-soluble resulting in drug delivery. For example, medications are commonly coated with enteric coatings which are water-insoluble at the acidic pH of the stomach and water-soluble in the basic pH of the intestine.

U.S. patent application Ser. No. 08/695,237, filed Aug. 8, 1996 now U.S. Pat. No. 5,739,210, describes a new class of reversible block/graft copolymer surfactants that are inexpensively produced from polyethylene glycol (PEG) and polymethacrylic acid (PMAA) by free-radical polymerization, which disclosure is incorporated herein by reference. These copolymers consist of a polymeric backbone with oligomeric grafts extending linearly from the backbone and are used for purposes unrelated to aphrons. The graft side chains are capable of forming hydrogen-bonded complexes with the backbone under acidic conditions to form blocks of hydrophilic and relatively hydrophobic polymer. The complex is hydrophobic because the hydrophilic acid and ether moieties are associated with one another, and are therefore unavailable to interact with the solvent; these hydrophilic groups are effectively buried in the complex, and only the hydrophobic methyl and ethylene groups are available to interact with the solvent. The copolymers assume a multiblock architecture with alternating hydrophilic and hydrophobic blocks under complex-promoting, acidic conditions, and revert back to a hydrophilic graft copolymer when the complex is broken (basic conditions). There is a need for a method and compositions which provide reversible aphrons.

OBJECTS

It is an object of the present invention to provide compositions which are a fine dispersion of a fluid phase in a second, immiscible phase using CGA or CLA so that the stability properties of the dispersion can be controlled by manipulating a change of environmental condition of the aphrons, particularly pH. In this way, the dispersion of CGA or CLA can be maintained stable during the phase-contacting step and then quickly coalesced for phase separation. It is further an object of the present invention to provide a method of producing the dispersions of CGA and CLA, maintaining them stable for a desired period of time, and then coalescing them. It is further an object to provide the dispersions by contacting the immiscible fluid phases, together with a novel, reversible, polymeric surfactant, in a high shear zone wherein dispersions are coalesced by making a small, predetermined change in pH. These and other objects will become increasingly apparent by reference to the fop owing description and the drawings.

DESCRIPTION OF PREFERRED EMBODIMENTS

Figure 1:
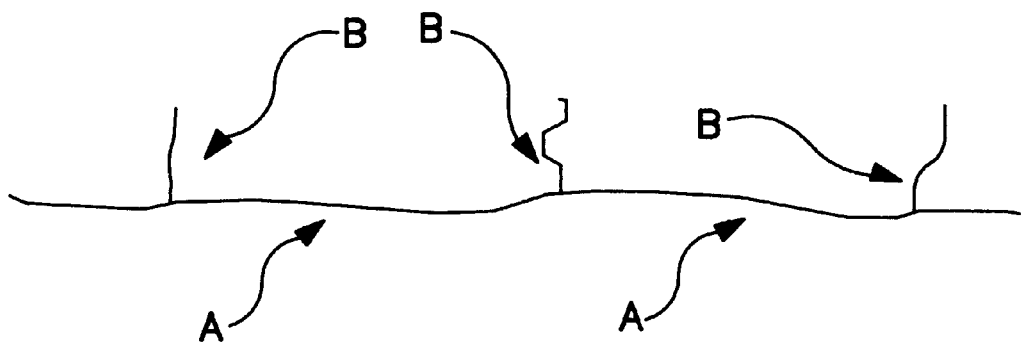
FIGS. 1A and 1B are schematic molecular drawings showing the preferred polymer under basic conditions for coalescing the aphrons (FIG. 1A) and under acidic conditions for forming the aphrons (FIG. 1B).
Figure 1:
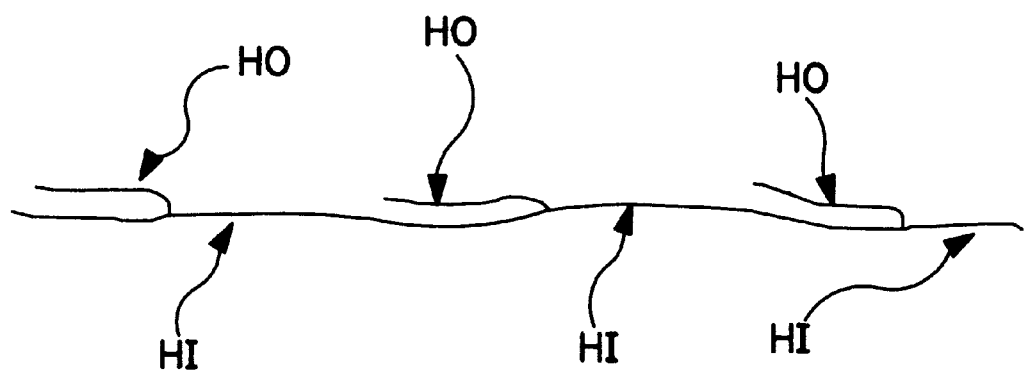

The present invention relates to a method for reversibly forming and then coalescing liquid or gas aphrons in an aqueous liquid which comprises:

(a) providing a chemical selected from the group consisting of an emulsifier, surfactant or mixtures thereof in the aqueous liquid wherein the chemical is reversibly rendered hydrophobic, amphipathic, or hydrophilic as a function of a change of condition of the aqueous liquid which changes a physical structure of the chemical;

(b) forming aphrons in the aqueous solution of the chemical at a first condition where the chemical stabilizes the aphrons in the aqueous solution; and (c) changing the conditions in the aqueous solution so that the aphrons are coalesced.

Further, the present invention relates to a method for separating a chemical:

(a) forming aphrons in an aqueous liquid wherein a chemical used for forming the aphrons is selected from the group consisting of an emulsifer, a surfactant and mixtures thereof is reversibly hydrophobic, amphipathic or hydrophilic as a function of a change of condition of the aqueous liquid which changes a physical structure of the chemical;

(b) contacting the aphrons with a separate liquid so that there is a transfer of a chemical between the liquids;

(c) changing the conditions of the aqueous liquid to coalesce the aphrons; and (d) separating the chemical from the liquid containing the chemical.

Further still, the present invention relates to a method of transferring a gas or liquid which comprises:

(a) forming aphrons in an aqueous liquid, wherein a chemical used for forming the aphrons is selected from the group consisting of an emulsifier, a surfactant and mixtures thereof which is reversibly hydrophobic, amphipathic, or hydrophilic as a function of a change of condition of the aqueous liquid which changes a physical structure of the chemical;

(b) contacting the aphrons with a separate liquid so that there is a transfer of a gas or liquid from the aphron between the liquids; and (c) changing the condition of the aqueous liquid to coalesce the aphrons.

Finally, the present invention relates to a composition which comprises:

(a) a gas or a liquid; and (b) aphrons containing the gas or liquid, wherein the aphrons are formed in an aqueous liquid containing a chemical selected from the group consisting of an emulsifier, a surfactant and mixtures thereof which is reversibly hydrophobic, amphipathic or hydrophilic as a function of a change of condition of the aqueous liquid which changes a physical structure of the chemical and wherein the aphrons are coalesced by the change of condition of the aqueous liquid.

An "emulsifier" is defined as a chemical which stabilizes one liquid phase which is insoluble in a second liquid phase to form a stable dispersion. A "surfactant" is defined as a surface active agent which reduces the surface tension of a liquid. The surfactant or emulsifier can operate by forming aphrons at a low pH where the aphrons are coalesced at higher pH. It is also the case that the surfactants can be synthesized so that the reverse is the case, i.e. that the aphrons are coalesced at low pH and maintained at a higher pH. The surfactant or emulsifier can be hydrophobic, amphipathic or hydrophilic and can be either in the aqueous phase or in the water insoluble phase in order to provide the aphrons.

This invention provides a method for producing a fine dispersion of immiscible fluid phases, whose stability properties can be readily controlled by small adjustments in environmental conditions, particularly pH, which change a physical structure of a surfactant. Such dispersions provide extremely high surface areas between the immiscible phases, yet allow rapid coalescence and phase separation on demand. These features are valuable in several classes of industrial processes, including separation processes, multiphase chemical and biochemical reaction systems, and environmental remediation as discussed above. The method uses a high-shear mechanical processing step, together with the reversible polymers, whose surfactant properties depend on pH.

In the preferred embodiment, a liquid phase is contacted with either a gas phase or a second liquid phase immiscible with the first in a high-shear zone under pH conditions that induce the polymer to have surfactant properties. The shear creates a fine dispersion of the immiscible phases, which would be stabilized by the polymer. The shear is achieved in a variety of ways, including mechanical agitation or forced flow through a small orifice or venturi. When it is desirable to promote coalescence of the dispersed phase or to induce the polymer to leave the interface, the pH is changed such that the surfactant or emulsifying properties of the polymer are reduced. The pH influences the degree of reversible intramolecular complexing between segments of the polymer. The degree of complexation, in turn, determines whether the reversible polymer is hydrophilic, hydrophobic, or amphiphilic.

The present invention uses a preferred class of polymers comprising reversible hydrophobic functionalities. In a preferred embodiment, the polymers comprise about 1% to about 95% hydrophilic segments comprising Lewis base functional groups (B segments), and about 5% to about 99% hydrophilic segments comprising Lewis acid functional groups (A segments). By themselves, the A and B segments are water-soluble or water-swellable. When combined under appropriate conditions, portions of the A and B segments are capable of forming water-insoluble complexes which can be reversibly broken or de-complexed via changes in pH, temperature or solvent polarity. This reversible complexation results in large changes in the polymer's solubility in water, and may be utilized to achieve large reversible changes in emulsion stability, solution or dispersion viscosity, particle size, permeability, equilibrium swelling, and the like.

The preferred class of polymers have the following formula:

where:

A=segment comprising Lewis acid functional group(s);

B=segment comprising Lewis base functional group(s);

C=optional hydrophilic segment;

D=optional hydrophilic segment;

Xa—moles of A;

Xb=moles of B;

Xc=moles of C; and

Xd=moles of D;

As used herein, the term "hydrophilic segment" is meant to encompass a single hydrophilic group containing moiety or unit, as well as two or more repeating units which contain a hydrophilic group. Likewise, the term "hydrophobic segment" is meant to encompass a single hydrophobic group containing moiety or unit, as well as two or more repeating units which contain a hydrophobic group.

The preferred embodiment polymers of the present invention are graft or block copolymers which comprise A and B polymer segments or sequences that, under certain conditions, can be characterized as containing Lewis acid and Lewis base monomer repeating units, respectively. As previously noted, the A and B segments by themselves, are water-soluble or water-swellable. That is, the A or B segments, if not incorporated into a polymer, are water-soluble and so readily dissolve in an aqueous environment. The term "water-swellable" as used herein, means that the A or B segments, if not incorporated into the polymers described herein, can absorb or imbibe water to a degree of at least 50% of the weight of the respective A or B segment. A segments comprise Lewis acid monomer repeating units. "Lewis acid monomer repeating units" as that term is used herein, refers to one or more monomers having electron deficient hydrogen atoms and which are not ionized. Examples of A segments which include Lewis acid monomer repeating units include, but are not limited to, acrylic acid, methacrylic acid, itaconic acid, maleic acid and vinyl phenol in their protonated states, among others. Most preferred examples of A segments include acrylic acid and methacrylic acid. It is contemplated that the A segments may comprise combinations of the aforementioned units, or comprise combinations of those units with other monomers or groups. For example, the A segment could comprise one or more repeating units of a copolymer of acrylic acid and methacrylic acid, either by itself or in combination with other monomers or groups.

As noted, B segments generally comprise "Lewis base monomer repeating units." That term as used herein, refers to units that are not ionic, yet have some basic character. Examples of B segments which include Lewis base monomers include, but are not limited to, ethylene oxide, ethylene glycol, vinyl pyrrolidone, acrylamide monomers, or other alkylene oxides such as propylene oxide and butylene oxide, among others. Most preferred examples of B segments include segments having ethylene glycol monomer repeating units such as oligo(ethylene glycol) monomethacrylate having a nominal Mn of the ethylene glycol repeat unit ranging from about 200 to about 1000; and behenyl poly(ethylene oxide) methacrylate having a nominal Mn of ethylene oxide chain of about 1100. A previously noted with regard to the A segments, it is also contemplated that the B segments may comprise combinations of the aforementioned units, or comprise combinations of those units with other monomers or groups.

The preferred embodiment polymers of the present invention comprise about 0k to about 95% (all percentages expressed herein are mole percentages except if noted otherwise) B segments, and about 5% to about 99% A segments. The preferred embodiment polymers further comprise A segments and B segments in particular ratios with respect to each other. The preferred molar ratio of A segments to B segments is from about 0.01:1 to about 100:1.

Segment C is a hydrophilic monomer. It is optional to include segment C in the polymers of the present invention. An example of segment C is 2-acrylamido-2-propane sulfonic acid. The amount of C segments in the preferred embodiment polymers ranges from about 0 to about 10% of the total A segments in the polymer. As previously noted with regard to the A and B segments, the C segment may also comprise more than one type of monomer.

Segment D is a hydrophobic monomer. The polymers of the present invention optionally contain segment D. Examples of segment D include, but are not limited to, lauryl methacrylate or lauryl acrylate. The amount of D segments in the preferred embodiment polymers ranges from about 0 to about 10% of the total A segments in the polymer. As previously noted in the discussion of the A and B segments, the D segment may also comprise more than one type of monomer.

The preferred embodiment polymers comprise a backbone formed primarily from hydrophilic A segments, and branches or grafts that are primarily hydrophilic B segments. The preferred embodiment polymers may further comprise minute amounts of optional segments C and D. As described in greater detail below, segments A and B form a stable hydrophobic complex under acidic conditions while the complex is broken under basic conditions resulting in a hydrophilic polymer.

It should be noted that repeating units such as acrylic acid or methacrylic acid can be transformed from their Lewis acid form (protonated) to a basic form (ionized, neutralized) by increasing aqueous phase pH, from acidic to basic. Thus, complexation between poly(acrylic acid) and poly(ethylene glycol) sequences is reversible and pH-sensitive, with acid-base complexes forming at acidic pH and breaking at basic pH. The resulting copolymers form intramolecular complexes under acidic conditions between the acrylic acid and ethylene glycol repeating units in water. If the Lewis acid and Lewis base monomer repeating units are present in a stoichiometric 1:1 molar ratio, then the polymer will precipitate in water.

The copolymers of this invention are generally prepared by polymerization in an aqueous medium under complex promoting conditions. The preferred embodiment polymers of the present invention can be prepared via free radical polymerization to produce block or graft polymers. Preferably, they are prepared via copolymerization of vinyl Lewis acid monomers with macromonomers containing a sequence of Lewis base monomers. For example, copolymers of the present invention can be formed by copolymerizing ethylenically unsaturated monocarboxylic acid with macromonomers comprising ethylenically unsaturated esters of a monocarboxylic acid, esterified with a poly(alkylene oxide), such as poly(ethylene oxide). The polymers of the present invention may also be synthesized by solution polymerization in alcohol/water mixtures or by emulsion polymerization in water under complex-promoting conditions. In particular, the Lewis acid monomers, e.g. acrylic or methacrylic acid, can be copolymerized with the Lewis base macromonomer poly(ethylene glycol monomethyl ether) methacrylate using hydrogen peroxide in a 1:1 ethanol:water mixture to form poly(acrylic acid) with poly(ethylene glycol) grafts. Alternatively, Lewis acid monomers can be polymerized in the presence of a Lewis base oligomer (such as polyethylene glycol with a molecular weight greater than 2,000 or a polyethylene glycol sequence which is part of a larger molecular) without the use of a macromonomer. In this case, the integrity of the polymer colloid is maintained primarily by intermolecular complexes (alkyl some grafting of the acid monomer onto the polyethylene glycol can occur) without requiring the use of a macromonomer.

Complexing polymers of the present invention can be readily identified using a simple solubility or swelling test. If the parent polymers are independently water-soluble, or swell in water to a certain extent, while the copolymer is water-insoluble or swells to a significantly lower extent under otherwise identical conditions, then complexation is occurring. For example, poly(acrylic acid) and poly(ethylene glycol) are each water-soluble at acidic pH. However, the stoichiometric copolymer containing a 1:1 monomer repeating unit ratio of acrylic acid and poly(ethylene glycol methacrylate) is water-insoluble. Thus, complexation is occurring. If methacrylic acid is substituted for acrylic acid, the poly(methacrylic acid) is not water-soluble but has a very high water uptake (~90%) under acidic conditions. In contrast, the stoichiometric copolymer with poly(ethylene glycol methacrylate) has a very low water uptake (less than 25 wt %).

FIGS. 1A and 1B illustrate the reversible configurations of the polymers of the present invention. FIG. 1A illustrates a copolymer comprising a backbone of primarily A segments and a plurality of branching B segments disposed along the polymer backbone. In the uncomplexed state generally depicted in FIG. 1A, all portions of the polymer are hydrophilic and the polymer exhibits a particular set of properties or characteristics at that state. When in its complexed state as illustrated in FIG. 1B, the B segments complex with A segments along the polymer backbone. The resulting complexation causes previously hydrophilic portions of the polymer i.e. B segments and those A segments that complex with the B segments, to become hydrophobic, designated as HO in FIG. 2. Depending upon the ratio of B segments to A segments, and length or configurations of B segments, portions of the polymer may remain "exposed" when the polymer is in its complexed state. Such exposed regions are still hydrophilic and are designated in FIG. 1B as HI.

Figure 2:
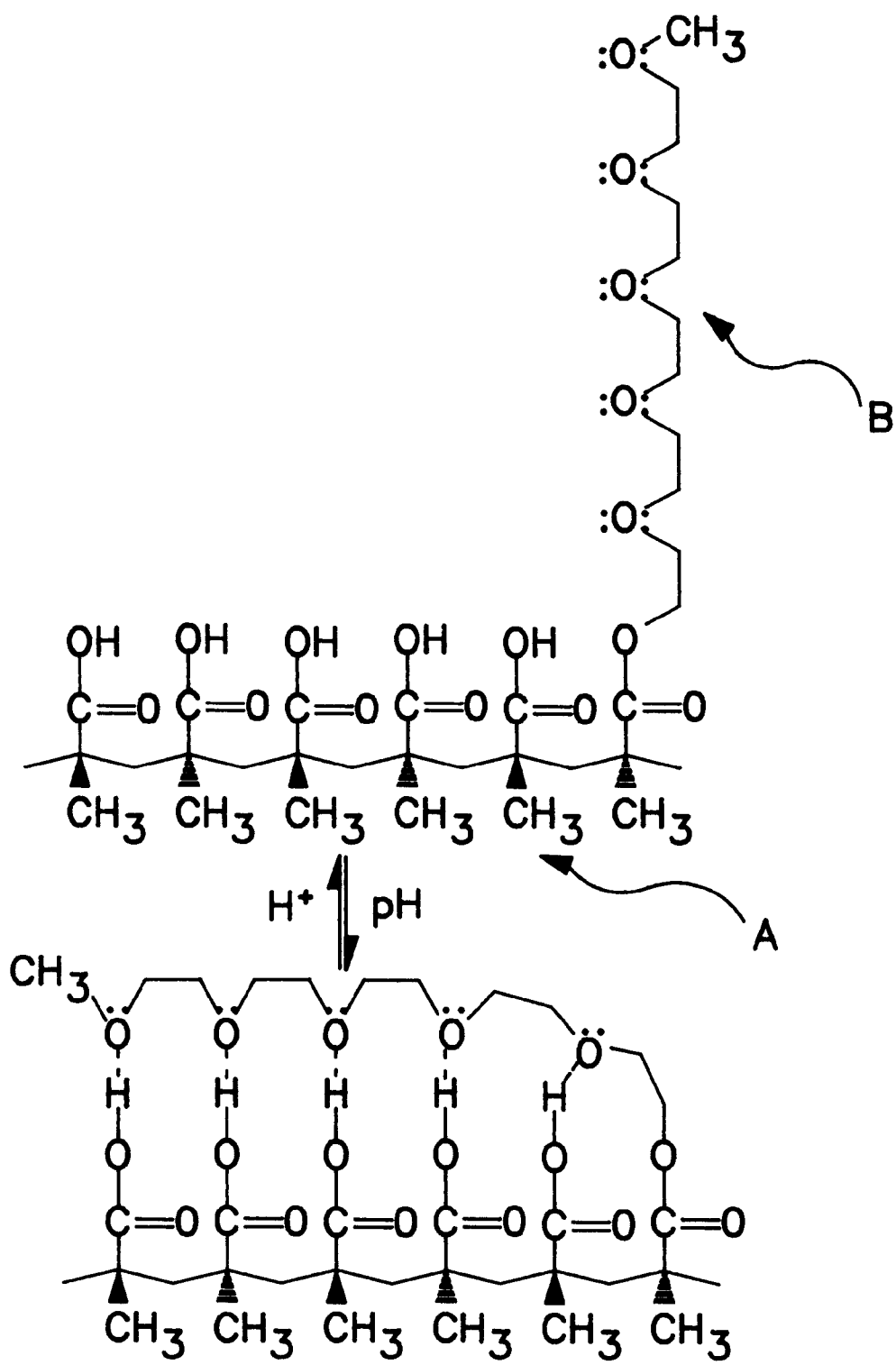
FIG. 2 is a chemical molecular drawing showing a hydrogen bonding and unbonding mechanism of the block copolymer.

FIG. 2 illustrates in greater detail the complexation occurring between A and B segments of a preferred embodiment polymer of the present invention. In this scheme, complexation occurs via hydrogen bonding along the respective segments at acidic conditions.

Nonstoichiometric complexing polymers of the present invention are useful as reversible emulsifiers. Under complex promoting conditions, the polymers assume an amphiphathic structure, with hydrophilic (noncomplexed) regions and water-insoluble hydrophobic region, as illustrated in FIGS. 1B and 2. These materials are capable of forming highly stable emulsions of oil in water. When the complexes are broken, such as via a pH change, the polymers become completely hydrophilic and the emulsions break. Thus, the polymers of the present invention comprise reversible hydrophobic groups and do not require an inherently hydrophobic group.

The techniques and polymers of the present invention can also enable production of copolymers of acrylic acid or methacrylic acid, and long chain polyethylene glycol via suspension polymerization in an aqueous environment. Conventional suspension polymerization of polyethylene glycol and acrylic acid or methacrylic acid require each reactant macromolecule be hydrophilic. The intermediate reaction product is relatively hydrophobic, and so an organic solvent must be used to sustain the resulting dispersion. The present invention enables the formation of microparticles of the resulting polymeric product in an aqueous environment without the necessity of an organic solvent.

The preferred reversible surfactant was produced using inexpensive, free-radical polymerization of polyethylene glycol and polymethacrylic acid. These precursors are environmentally friendly and have received FDA approval for a variety of uses (Greenwald and Lusking, Poly(Acrylic Acid) and its homologs in: Handbook of Water-soluble Gums and Resins, Robert L. Davidson, Ed., McGraw hill, New York, N.Y. 17–18 (1980)). The molecular structure of the polymeric surfactant is shown in FIGS. 1A, 1B and 2.

The Examples show that the polymeric surfactants produce aphrons and the resulting aphrons can be rapidly coalesced (destroyed) by small changes in pH. The protocol described by Bredwell et al, (App Biochem. Biotechnol., 51/52, 501–509 (1995)) was used to measure the rate of formation and stability of CGA dispersions at pH values of 3, where the polymer behaves as a surfactant or emulsifier, and 7, where its surfactant properties are lost. Excellent CGA dispersions were obtained at a pH of 3, even for surfactant concentrations less than 0.1% by weight, but not at pH of 7 for the preferred poly(ethylene)glycol graft with a poly(methacrylic acid) backbone (FIG. 2). Samples of the resulting CGA dispersion were then pumped into buffer solutions maintained at different pH values. At a buffer pH of 3, the foam remained quite stable, retaining half its original volume for over 30 minutes. In contrast, at a buffer pH of 7, the foam virtually disappeared within 20 seconds. Additional studies confirmed that a 0.1.% by weight aqueous surfactant solution could reversibly emulsify 20% by volume methyl laurate under acidic conditions. The resulting emulsion was rapidly broken simply by raising the pH. Essentially none of the methyl laurate was emulsified under basic conditions. The emulsification properties were found to be fully reversible during repetitive pH cycles.

EXAMPLE 1

This example shows the general process preparation of solution containing polymers with reversible hydrophobic functionalities.

Four grams of the emulsifier (also referred to as surfactant), a graft copolymer composed of methacrylic acid (MAA) and polyethylene glycol (PEG) prepared by the process described in U.S. application Ser. No. 08/695,237, filed Aug. 8, 1996 now U.S. Pat. No. 5,739,210, which is incorporated herein by reference, were added to 1.5 L of reverse-osmosis (RO) water to give a 0.27% by weight solution. The polymer was identified as "10:1 MAA/PEG, 48 $\mu$L $H_2O_2$ (50%)". The $H_2O_2$ is a free radical initiator. The solution was mixed using a magnetic stirring bar for about 24 hours. At that time it had not yet fully dissolved. The pH was adjusted upward from about 3 to 4.0 using NaOH, and the solution was stirred until the polymer was completely dissolved. A slight turbidity (0.002 ODU at 600 nm vs. distilled water) of the solution at this pH suggested that the critical micelle concentration was exceeded at this concentration.

EXAMPLE 2

The surfactant was successfully used to produce high-quality CGA dispersions at surfactant concentrations as less than 0.1% by weight, using the protocol of Bredwell et al., App. Biochem. Biotechnol., 51/52:501–509 (1995). The gas fractions of these dispersions, as measured by drainage in a graduated cylinder, are shown in Table 1.

TABLE 1

| Surfactant concentration | pH | Gas volume fraction |
|---|---|---|
| 0.27% | 4 | 0.58 |
| 0.27% | 3 | 0.71 |
| 0.089% | 3 | 0.64 |

EXAMPLE 3

The effect of pH on the coalescence properties of the dispersions of Example 2 was then tested. A stream of CGA produced using a 0.089% surfactant solution at a pH of 3.0 was pumped into phosphate buffer at different pH values. At a buffer pH of 3.0, the foam remained relatively stable, losing only half its volume over a 20 minute period. In contrast, at a pH of 7.0, the foam layer disappeared completely within 20 s. These results indicated that excellent CGA dispersions are produced with the polymer, even with surfactant concentrations less than 0.1% by weight, that the dispersions are stable enough to be pumped, and that pH adjustments can be used to coalesce the dispersions on demand.

EXAMPLE 4

The efficacy for waste-treatment applications using CGA and CLA produced from the reversible polymeric surfactants is tested. Methods have been developed by which enzymes suitable for bioremediation can be bound to PEG while retaining their activity (Woodward and Kaufman, Biotechnol. Bioeng. 52:423–428 (1996)). The PEG can serve to solubilize the enzyme in organic liquids or, alternatively, reversibly adsorb the enzyme to the interface of a CGA or CLA. Various contacting approaches are used in which PEG-bound enzymes are used for biocatalytic reactions involving an organic phase. For example, reversible CGA are used to remove PEG-bound hydrogenase enzyme from toluene following sulfur reduction. This approach allows enzymes used for bioremediation in organic liquids to be quickly recovered after the reaction step for reuse. In a second example, metals are precipitated from aqueous solution via formation of sulfide salts (Hammack et al., Wat. Res. 28:2321–2329 (1994)). An aqueous solution representative of a DOE liquid waste is treated with a gas phase containing $H_2S$.

EXAMPLE 5

The rates of metal precipitation are measured using both conventional gas sparging and CGA sparging. The sulfide used in this process is biogenically produced in a sulfate-reduction bioreactor. The results of these studies demonstrate the utility of reversible CGA and CLA as a versatile new, contacting technology for separations and waste-treatment applications.

EXAMPLE 6

Air and water is used to form the CGA, and oleyl alcohol and water is used to form the CLA. Oleyl alcohol is a non-toxic solvent that has been used effectively in extractive fermentations (Jones et al., Biotechnol. Letters 15:871–876 (1993)). The CGA is produced in a 5 L glass vessel containing baffles and a cylindrical rotor that is turned at several thousand rpm by a high-speed motor (Bredwell et al., App. Biochem. Biotechnol., 51/52:501–509 (1995)). The CLA is produced by adding drops of the nonpolar liquid phase to CGA produced as described above. The high surface area of the CGA facilitates spreading of the oil and formation of the CLA (Sebba, F., Foams and Biliquid Foams—aphrons, John Wiley and Sons, Ltd., New York 62–71; 103–106 (1987)).

EXAMPLE 7

The properties of the aphrons were measured as a function of the pH and the molecular architecture of the polymer. For CGA dispersions, the dependent variables are the rate of formation, the rate of coalescence and the size distribution. The formation was determined by recording the volume of the CGA dispersion inside the CGA generator as a function of time. The volume was easily observed through the transparent wall of the calibrated vessel. The coalescence rate was measured in two ways. In the first, the dispersion is poured into a graduated cylinder, and the levels of the liquid/CGA and CGA/air interfaces was recorded as a function of time (Bredwell et al., App. Biochem. Biotechnol., 51/52 501–509 (1995)). In the second, a known volume of the dispersion was placed in a closed, transparent chamber, and the particle-size distribution was measured as a function of time using the PDA. The effect of molecular architecture is explored by repeating these experiments for surfactants differing in the length of the polymer backbone, density of grafts and the like.

EXAMPLE 8

Formation of CLA dispersions requires the use of two surfactants or emulsifiers: one water-soluble and the other soluble in the nonpolar phase (Sebba, Foams and Biliquid Foams—aphrons, John Wiley and Sons, Ltd., New York (1987)). To address the question of whether both surfactants need to be reversible to induce coalescence via pH changes, different combinations of reversible and conventional surfactants were tested. The rate of CLA formation was measured by the rate at which the nonpolar phase can be added without the formation of a nondispersed nonpolar phase. The volume fraction of the nonpolar phase was calculated from the volumes of the aqueous and nonpolar phases added. The stability is evaluated either using the PDA or by filing a graduated cylinder with CLA dispersion and recording the liquid/CLA and CLA/air volumes over a period of several days. The CLA dispersions were extremely stable and settle slowly. Consequently, little phase separation is expected without destabilizing the dispersion via pH adjustment.

EXAMPLE 9

The rate of coalescence of CGA and CLA in buffer is measured. For the CGA dispersions, the independent variables is the pH of the buffer and the molecular architecture of the polymer. The CGA dispersion is pumped from the CGA generator into a volume-calibrated stirred tank containing phosphate buffer at the target pH. The levels of the liquid/CGA and CGA/air interfaces is then recorded as a function of time. When coalescence is rapid, the experiments are videotapes with a stopwatch attached to the tank; then the tape will be replayed to record the data. Experiments are carried out in a transparent reservoir using the PDA.

EXAMPLE 10

Analogous experiments are conducted for the CLA. The independent variables are the pH of the buffer and the molecular properties of the surfactants. A known volume of CLA is dispersed into phosphate buffer in a graduated cylinder. The levels of the buffer/CLA and CLA/nonpolar liquid levels are then recorded as a function of time. Qualitative observations regarding the different types of phase behavior are also recorded. Demonstration of pH-induced coalescence of CLA is an important objective of these experiments. The PDA is also used in instances when the CLA coalesce relatively rapidly (i.e., on a time scale of minutes to hours).

EXAMPLE 11

1.0 g of LB Medium mix (Sigma Chemical Co.) was dissolved into 50 mL of the surfactant solution, and the pH of the resulting solution was titrated to pH=7.0 using NaOH. The slight turbidity previously noted disappeared at this pH, suggesting that the surfactant properties had been changed and that a significant micelle concentration no longer existed. A second solution was prepared that was identical, except that it lacked the surfactant. The initial OD (600 nm) values of the solutions were 0.018 vs distilled water. The solutions were transferred to 125 mL Erlenmeyer flasks and inoculated with 2.5 mL of an overnight culture of an *Escherichia coli* EC423 (EC423 is available from Dr. Pat Oriel at Michigan State University, East Lansing, Mich.). The initial optical density of the solutions was 0.24. Both flasks were capped with foam plugs and incubated at 37° C. with 150 rpm shaking. The next day, heavy cell growth was apparent in both flasks. The optical density of the two cultures, is given below. Samples were diluted three-fold with M9 buffer and five-fold for the 19 h and 25 h times, respectively. The raw data were then multiplied by the dilution factor to give the results in Table 2.

TABLE 2

| Time (h) | LB[1] solution with surfactant | LB solution |
| --- | --- | --- |
| 0 | 0.24 | 0.24 |
| 19 | 3.5 | 3.7 |
| 25 | 4.4 | 4.5 |

[1]Sigma Chemical Co.

These results indicate that the surfactant did not significantly inhibit *E. coli* growth at a concentration of 0.27% in LB medium at pH=7.0.

EXAMPLE 12

The microbubble generator described by Bredwell et al. (App. Biochem. Biotechnol., 51/52, 501–509 (1995)) was used to form microbubbles from about 1.5 L of the surfactant solution. The foam level in the microbubble generator vessel was recorded as a function of time after the generator was activated. The resulting foam was then transferred to a 1000 mL graduated cylinder. The stability of the foam drainage was monitored by recording the level of the foam/air interface and the liquid/foam interface as a function of time. The gas fraction of the foam was calculated from the initial volume of the foam and the final liquid volume after the foam had fully disintegrated. The surfactant solution was then titrated to pH=7.0 using NaOH, and the experiment was then repeated. Finally, the pH of the surfactant solution was adjusted to pH=3.0 using HCl, and the experiment was repeated.

Figure 3:
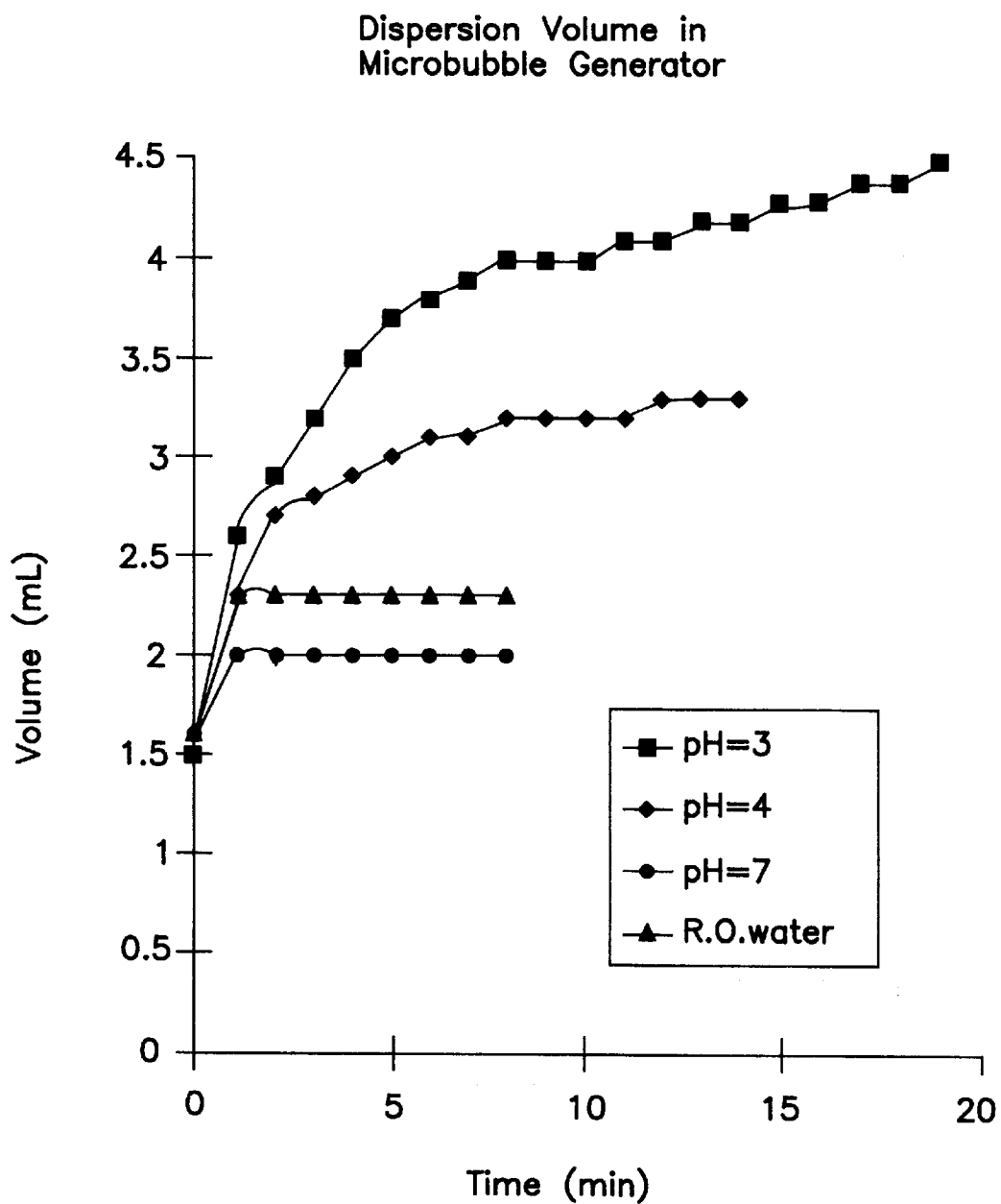
FIG. 3 is a graph showing volume of gas-liquid dispersion in a CGA generator as a function of time.

The gas-liquid-dispersion expansion data are shown in FIG. 3. The expansion properties of RO water are also shown, for comparison. Neither the pH=7 nor the RO water experiments showed significant increase in foam volume beyond the initial value. However, the pH=4 and pH=3 runs exhibited an increase in expansion over time. The pH=3 run exhibited an expansion of at least three-fold, which was the upper bound reported by Bredwell et al. (App. Biochem. Biotechnol. 51/52, 501–509 (1995)) for conventional-surfactant foams. Based on the initial and final volumes, the expansions for pH=7.4, and 3, were 25%, 106% and 200%, respectively. One run was also performed with the surfactant solution diluted by a factor of 3 (to 0.089% by weight) using RO water and pH adjusted back to 3.0. This solution exhibited an expansion of 153%.

EXAMPLE 13

The stability properties of the dispersions were readily measured for pH 4.0 and 3.0, but not for the pH=7.0 case. At the latter pH, there was no clear interface between the gas-liquid dispersion and the underlying liquid phase. Early in the experiment, the interface was measured within a range, but as time went on, the interface got more and more difficult to identify. This effect was attributed to the significantly higher viscosity of the solution at the higher pH, which slowed down the relative motion between the bubbles and the liquid. Nevertheless, the gas fraction of the dispersions was able to be measured based on the initial volume of the dispersion and the final liquid volume after drainage was complete. These values are given below, in Table 3. The dispersion of air in RO water coalesced completely before it could be transferred to the graduated cylinder.

TABLE 3

Gas fraction based on dispersion settling data

| Liquid phase | Gas volume fraction |
| --- | --- |
| RO Water | 0 |
| Surfactant solution, pH = 7 (0.27%) | 0.26 |
| Surfactant solution, pH = 4 (0.27%) | 0.58 |
| Surfactant solution, pH = 3 (0.27%) | 0.71 |
| Surfactant solution, pH = 3 (0.089%) | 0.64 |

The foam at a pH of 3.0 exhibited some solid character, reminiscent of meringue. This effect was more pronounced at the higher concentration. After the foam was formed in the microbubble generator, it was transferred to the graduated cylinder in part by pouring and in part using a spatula. A variety of surfaceactive compounds, including proteins and polysaccharides, have been observed to form a gel-like film at the bubble interface that inhibits hole nucleation between adjacent bubbles and thus stabilized foams. The surfactant apparently also exhibits this property to some degree. A 30 mL beaker was filled to the top with a relatively dry pH=3.0 foam. A drop of 1 M NaOH was then placed on the top of the foam. The portion of the foam in contact with the drop instantly began to retract. As the bubbles burst, new portions of the foam were exposed to the NaOH. Within 30 seconds, 90% of the foam had disappeared. Without the addition of the foam, the half life of this foam was on the order of 30 minutes. These observations are consistent with the pH-reversible nature of the surfactant.

EXAMPLE 14

The microbubble dispersions formed using the reversible surfactant solution could be pumped into a fermenter and induced to coalesce by manipulating the pH of the fermentation medium. The system consisted of the microbubble generator, a peristaltic pump, and a MULTIGEN fermenter system (New Brunswick, Scientific). The pump was used to deliver microbubbles from the microbubble generator to the fermenter. The simulated fermentation medium consisted of 10 g of $KH_2PO_4$ in 500 mL of RO water. The pH of the solution was adjusted to 3.0 using HCl.

The microbubbles were formed using 1.5 L of 0.089% surfactant solution at a pH of 3.0. The microbubble generator was allowed to run until the foam volume reached its steady-state volume of about 3.7 L. During this time, the peristaltic pump withdrew microbubbles from the 1 L level in the generator, and recycled them back to the generator. The experiment was initiated by switching the microbubble stream to the fermenter. The microbubbles entered the medium through several holes near the bottom of the impeller shaft. The single, RUSHTON impeller was mounted just above these holes to disperse the microbubbles throughout the liquid phase. An impeller rate of 100 rpm was used. The microbubble flow rate was measured to be 0.6 L/min using a graduated cylinder. The microbubbles were delivered into the liquid medium for 30 s, and then the levels of the liquid/foam interface and foam/air interface were recorded as a function of time.

The experiment was then repeated under identical conditions, except that the pH of the liquid medium in the fermenter was titrated to 7.0 (using NaOH) instead of 3.0. Fresh medium was prepared for this experiment, rather than reusing that from the pH=7 experiment. The experimental data are presented in FIG. 4 as volume of foam on top of the liquid as a function of time. The half time of the foam for the pH=3.0 experiment was about 30 minutes, whereas, the foam was essentially gone within 20 s for the pH=7 case. These results indicate that the pH of the liquid phase can be effectively used to destabilize the microbubbles produced using this surfactant. Also, the results verify that the microbubble dispersion produced under these conditions can be readily produced and pumped to a remote fermenter.

EXAMPLE 15

Several sequential runs were performed using the same pH=7 medium to see to what extent the small amount of the pH=3 surfactant added with the microbubbles influenced the pH of the medium. In each run, microbubbles were added for 30 s. The volume of liquid contained in the foam was about 150 mL per run. The liquid volume and pH before and after each run was measured, and the pH of the medium was measured periodically. The data are recorded in Table 4. Between Runs 3 and 4, a portion of the liquid medium was poured out, reducing the liquid volume back to 500 mL.

TABLE 4

Liquid volume and pH data for sequential runs at pH = 7 medium and pH = 3 foam

| Run | Initial volume (mL) | Final volume (mL) | Initial pH | Final pH |
|-----|---------------------|-------------------|------------|----------|
| 1   | 500                 | 650               | 7.0        |          |
| 2   | 630                 | 800               | 7.04       |          |
| 3   | 790                 | 960               |            | 7.00     |
| 4   | 510                 | 700               | 7.00       | 6.92     |

Collectively, 660 mL of the pH=3 surfactant solution were added via the microbubble sparging to an initial volume of 500 mL of the pH=7 medium. The total change in pH was on the order of 0.1 pH unit, indicating that the charge density of the methacrylic acid groups was quite small relative to the buffering capacity of the medium. This observation is consistent with the very low surfactant concentration (0.089% by weight) used to create the microbubble dispersion. A portion of the pH change may also be due to sample dilution of the buffer in the medium by the surfactant solution. These results indicate that the little additional titrant should be needed to counteract any acidification resulting from addition of a pH=3 surfactant.

In Run 1, the foam was observed to disappear from the top of the liquid within 20 seconds after the sparging was terminated. In Run 4, the foam was essentially gone within a minute. Accumulation of the surfactant in the fermenter and possibly dilution of the buffer in the solution may have slowed down the rate of foam disappearance slightly, but the rate is still more than an order of magnitude faster than when the medium was maintained at pH of 3. Thus, even when volume of surfactant liquid exceeding the initial volume of the fermentation is added, the foam is effectively controlled by the reversible feature of the surfactant.

EXAMPLE 16

Figure 4:
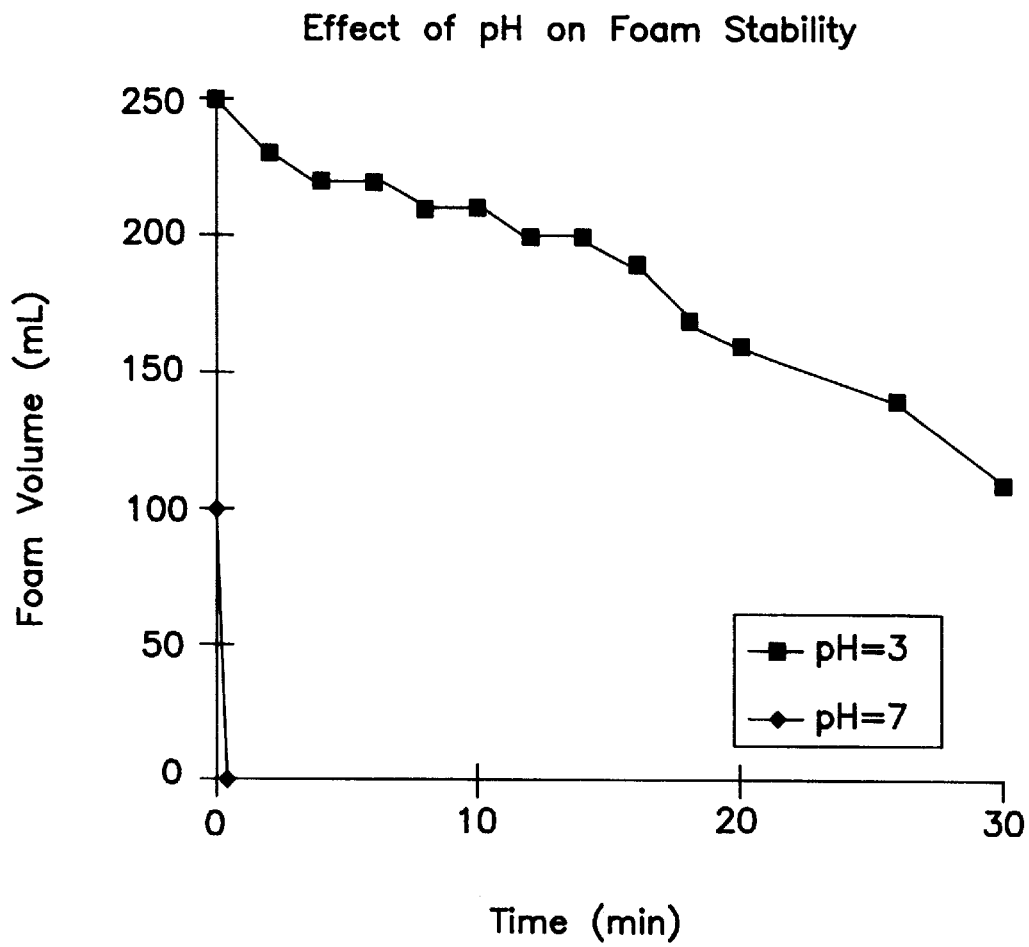
FIG. 4 is a graph showing the effect of pH on foam volume as a function of time.

The poly(methacrylic acid-g-ethylene glycol) copolymers described previously exhibits surfactant or emulsifier properties at low pH, but allows the dispersions to be destabilized at higher pH values (recall FIGS. 2–4). A similar synthetic scheme can be used to synthesize surfactants that exhibit the opposite behavior. It has been shown that by including an oligomeric hydrophobic monomer (lauryl methacrylate) in the reaction mixture, and by using an MAA/EG repeat unit ratio close to 1:1, the resulting copolymers exhibit emulsifier/surfactant properties under basic conditions, but allow the dispersions to be broken under acidic conditions. This behavior is explained by the rfact that under complex-promoting (acidic) conditions, the polymer is completely hydrophobic (all MAA and EG units form complexes with one another, and the lauryl methacrylate grafts are also hydrophobic). Therefore, under acidic conditions the polymers will partition into the hydrophobic phase. In contrast, under basic conditions, the complex is broken, and the polymer contains a hydrophilic PMAA backbone along with hydrophilic PEG grafts and hydrophobic grafts from the lauryl chains. Hence the graft copolymer is surface-active under basic conditions with the hydrophobic grafts partitioning into the lyophilic (oil) phase and the hydrophilic backbone and grafts extending into the aqueous phase. These graft copolymers are synthesized using the same general procedure described above (using the same solvent, initiators, temperature) with the addition of the lauryl methacrylate monomer. Systematic studies can be performed to determine the effects of the hydrophobic graft length and the ratio of hydrophilic to hydrophobic grafts on the performance of the surfactants/emulsifiers.

EXAMPLE 17

Synthesis gas, which consists primarily of carbon monoxide (CO) and hydrogen ($H_2$), is produced by the partial oxidation of an organic feedstock at high temperature in the presence of steam. Biomass is an excellent raw material for synthesis-gas production, and several new biomass-gasification plants have been built recently. Fermentation offers advantages over conventional catalytic conversion of synthesis gas, including lower operating temperatures and pressures, higher reaction specificity of the biological catalysts, and higher tolerance to sulfur compounds. A major impediment to the commercial development of synthesis-gas fermentations is low bioreactor productivity, due to the slow rate of mass transfer of the CO and $H_2$ into the liquid phase. The mass-transfer rate can be increased by increasing the agitator power input. However, this approach would not be feasible at the commercial scale, because power consumption increases with the impeller diameter to the fifth power and the impeller rate to the third power. The reversible aphrons are used to form the aphrons which increases the mass transfer rate and reduces the power input.

The foregoing description is only illustrative of the present invention and the present invention is limited only by the hereinafter appended claims.

We claim:

1. A method for reversibly forming and then coalescing gas containing aphrons in an aqueous liquid which comprises:
   (a) providing a chemical selected from the group consisting of an emulsifier, surfactant and mixtures thereof in the aqueous liquid wherein the chemical is reversibly rendered hydrophobic, amphipathic or hydrophilic as a function of a change of condition of the aqueous liquid which changes a physical structure of the chemical;
   (b) forming gas containing aphrons in the aqueous solution of the chemical at a first condition where the chemical stabilizes the gas containing aphrons in the aqueous solution; and
   (c) changing the conditions in the aqueous solution so that the gas containing aphrons are coalesced.

2. The method of claim 1 wherein the aphrons contain air as the gas.

3. The method of claim 1 wherein the surfactant comprises a graft copolymer of poly(acrylic acid) and poly (ethylene glycol).

4. The method of any one of claims 1, 2 or 3 wherein the change of condition is a change of pH.

5. The method of claim 3 wherein there is a molar ratio of between about 50 to 1 and 3 to 1 of (acrylic acid) repeat units and (ethylene glycol) repeat units.

6. A method for separating a chemical which comprises:
   (a) forming gas containing aphrons in an aqueous liquid wherein a chemical used for forming the aphrons selected from the group consisting of an emulsifier, a surfactant and mixtures thereof is reversibly hydrophobic, amphipathic or hydrophilic as a function of a change of condition of the aqueous liquid which changes a physical structure of the chemical;
   (b) contacting the gas containing aphrons with a separate liquid so that there is a transfer of a chemical between the liquids;
   (c) changing the conditions of the aqueous liquid to coalesce the gas containing aphrons; and (d) separating the chemical from the liquid containing the chemical.

7. The method of claim 6 wherein the aphrons contain air as the gas.

8. The method of claim 6 wherein the surfactant comprises a graft copolymer of poly(acrylic acid) and poly(ethylene glycol).

9. The method of any one of claims 6, 7 or 8, wherein the change of condition is a change of pH.

10. The method of claim 8 wherein there is a molar ratio of between about 50 to 1 and 3 to 1 of (acrylic acid) repeat units and (ethylene glycol) repeat units.

11. A method of transferring a gas which comprises:

(a) forming gas containing aphrons in an aqueous liquid, wherein a chemical used for forming the gas containing aphrons is selected from the group consisting of an emulsifier, a surfactant and mixtures thereof which is reversibly hydrophobic, amphipathic, or hydrophilic as a function of a change of condition of the aqueous liquid which changes a physical structure of the chemical;

(b) contacting the gas containing aphrons with a separate liquid so that there is a transfer of a gas between the aphron and the liquid; and (c) changing the condition of the aqueous liquid to coalesce the gas containing aphrons.

12. The method of claim 11 wherein the aphrons contain air as the gas.

13. The method of claim 11 wherein the surfactant comprises a graft copolymer of poly(acrylic acid) and polyethylene glycol).

14. The method of any one of claims 11, 12 or 13 wherein the change of condition is a change of pH.

15. The method of claim 13 wherein there is a molar ratio of between about 50 to 1 and 3 to 1 of (acrylic acid) repeat units and (ethylene glycol) repeat units.

16. The method of claim 11 wherein the transfer is provided in a fermentation using the gas aphrons.

17. The method of claim 16 wherein the transfer is of oxygen as the gas for the fermentation.

18. The method of claim 11 wherein the transfer is of a synthesis gas which is a mixture of carbon monoxide and hydrogen gases as the gas.

19. A composition which comprises:

(a) a gas; and (b) aphrons containing the gas, wherein the gas containing aphrons are formed in an aqueous liquid containing a chemical selected from the group consisting of an emulsifier, a surfactant and mixtures thereof which is reversibly hydrophobic, amphipathic or hydrophilic as a function of a change of condition of the aqueous liquid which changes a physical structure of the chemical and wherein the gas containing aphrons are capable of being coalesced by the change of condition of the aqueous liquid.

20. The composition of claim 19 wherein the surfactant comprises a graft copolymer of poly(acrylic acid) and poly(ethylene glycol).

21. The composition of claim 19 wherein there is a molar ratio of between about 50 to 1 and 3 to 1 of (acrylic acid) repeat units and (ethylene glycol) repeat units.

* * * * *